United States Patent [19]

Seubert et al.

[11] Patent Number: 5,721,130
[45] Date of Patent: Feb. 24, 1998

[54] ANTIBODIES AND FRAGMENTS THEREOF WHICH BIND THE CARBOXYL-TERMINUS OF AN AMINO-TERMINAL FRAGMENT OF βAPP

[75] Inventors: Peter A. Seubert, South San Francisco; Dale B. Schenk, Pacifica; Lawrence C. Fritz, San Francisco, all of Calif.

[73] Assignees: Athena Neurosciences, Inc., So. San Francisco, Calif.; Eli Lilly and Company, Indianapolis, Ind.

[21] Appl. No.: 440,423

[22] Filed: May 12, 1995

Related U.S. Application Data

[60] Division of Ser. No. 965,971, Oct. 26, 1992, Pat. No. 5,441,870, which is a continuation-in-part of Ser. No. 868,949, Apr. 15, 1992, abandoned.

[51] Int. Cl.$^6$ .................... C12N 5/12; A61K 39/395
[52] U.S. Cl. .................. 435/240.27; 435/70.21; 530/387.1; 530/387.9; 530/388.1; 530/389.1; 530/391.1; 530/391.3
[58] Field of Search .................. 530/387.1, 387.9, 530/388.1, 389.1, 391.1, 391.3; 435/70.21, 240.27; 436/547, 548

[56] References Cited

U.S. PATENT DOCUMENTS

| | | | |
|---|---|---|---|
| 4,666,829 | 5/1987 | Glenner et al. | 435/6 |
| 5,134,062 | 7/1992 | Blass | 435/7.21 |
| 5,200,339 | 4/1993 | Abraham | 435/23 |
| 5,234,814 | 8/1993 | Card et al. | 435/7.21 |
| 5,387,742 | 2/1995 | Cordell | 800/2 |

FOREIGN PATENT DOCUMENTS

| | | |
|---|---|---|
| 123527 | 10/1984 | European Pat. Off. |
| 171496 | 2/1986 | European Pat. Off. |
| 173494 | 3/1986 | European Pat. Off. |
| 184187 | 6/1986 | European Pat. Off. |
| 62-100291 | 5/1987 | Japan |
| WO 86/01533 | 3/1986 | WIPO |
| WO 87/02671 | 5/1987 | WIPO |
| WO 91/16628 | 10/1991 | WIPO |
| WO 91/19810 | 12/1991 | WIPO |
| WO 92/00521 | 1/1992 | WIPO |
| WO 92/09699 | 6/1992 | WIPO |

OTHER PUBLICATIONS

Harlow et al "Antibodies A Laboratory Manual" Published 1988 by Cold Spring Harbor Laboratories, pp. 74–76.

Henriksson et al, J. Neurochem 56: 1037–1042, 1991.

Palmert et al, Biochemical and Biophysical Research Communications, 165(1):182–188, 1989.

Higgins et al. (1994) Annals of Neurology 35:598–607. Transgenic Mouse Brain Histopathology Resembles Early Alzheimer's Disease.

Higgins et al. (1993) Annals New York Academy of Sciences 695:224–227. Transgenic Mice Expressing Human β–APP751, But Not Mice Expressing β–APP695, Display Early Alzheimer's Disease–like Histopathology.

Robakis et al. Soc. Neurosci. Oct. 26, 1993. Abstract No. 15.4, Anaheim, CA. An Alternative Secretase Cleavage Produces Soluble Alzheimer Amyloid Precursor Protein Containing a Potentially Amyloidogenic Sequence.

Seubert et al. (1993) Nature 361:260–263. Secretion of β–amyloid precursor protein cleaved at the amino terminus of the β–amyloid peptide.

Estus et al. (1992) Science 255:726–728. Potentially Amyloidogenic, Carboxyl–Terminal Derivatives of the Amyloid Protein Precursor.

Golde et al. (1992) Science 255:728–730. Processing of the Amyloid Protein Precursor to Potentially Amyloidogenic Derivatives.

Haass et al. (1992) Nature 359:322–325. Amyloid β–peptide is produced by cultured cells during normal metabolism.

Hyman et al. (1992) J. Neuropath. Exp. Neurol. 51:76. Kunitz Protease Inhibitor–Containing Amyloid β Protein Precursor Immunoreactivity in Alzheimer's Disease.

Kennedy et al. (1992) Neurodegeneration 1:59–64. Only Kunitz–Inhibitor–Containing Isoforms of Secreted Alzheimer Amyloid Precursor Show Amyloid Immunoreactivity in Normal Cerebrospinal Fluid.

Mullan et al. (1992) Nature Genet 1:345–347. A pathogenic mutation for probable Alzheimer's disease in the APP gene at the N–terminus of β–amyloid.

Seubert et al. (1992) Nature 359:325–327. Isolation and quantification of soluble Alzheimer's β–peptide from biological fluids.

Abraham et al. (1991) Biochem. Biophys. Res. Comm. 174:790–796. A Calcium–Activated Protease From Alzheimer's Disease Brain Cleaves At The N–Terminus Of The Amyloid β–Protein.

Chartier Harlan et al. (1991) Nature 353:844–846. Early–onset Alzheimer's disease caused by mutations at codon 717 of the β–amyloid precursor protein gene.

Goate et al. (1991) Nature 349:704–706. Segregation of a missense mutation in the amyloid precursor protein gene with familial Alzheimer's disease.

Murrell et al. (1991) Science 254:97–99. A Mutation in the Amyloid Precursor Protein Associated with Hereditary Alzheimer's Disease.

Quon et al. (1991) Nature 352:239–241. Formation of β–amyloid protein deposits in brains of transgenic mice.

(List continued on next page.)

Primary Examiner—Marianne P. Allen
Assistant Examiner—Patricia A. Duffy
Attorney, Agent, or Firm—John Storella; Jean Duvall

[57] ABSTRACT

Processing of β–amyloid precursor protein (βAPP) is monitored by detecting the secretion of a soluble βAPP fragment resulting from cleavage of βAPP at the amino-terminus of β–amyloid peptide. In vivo monitoring of secretion of the βAPP fragment may be monitored for diagnosis and prognosis of Alzheimer's disease and other β–amyloid-related diseases, while in vitro monitoring of such secretion from cultured cells may be monitored to identify inhibitors of β–amyloid production. The βAPP fragment may be detected using antibodies and other specific binding substances which recognize a carboxy-terminal residue on the fragment.

14 Claims, 4 Drawing Sheets

OTHER PUBLICATIONS

Esch et al. (1990) Science 248:1122–1124. Cleavage of Amyloid β Peptide During Constitutive Processing of Its Precursor.

Forss-Petter et al. (1990) Neuron 5:187–197. Transgenic Mice Expressing β–Galactosidase in Mature Neorons under Neuron–Specific Enolase Promoter Control.

Oltersdorf et al. (1990) J. Biol. Chem. 265:4492–4497. The Alzheimer's Amyloid Precursor Protein.

Oltersdorf et al. (1989) Nature 341:144. The secreted form of the Alzheimer's amyloid precursor protein with the Kunitz domain is protease nexin–II.

Palmert et al. (1989) Biochem. Biophys. Res. Comm. 165:182–188. Soluble Derivatives Of The βAmyloid Protein Precursor Of Alzheimer's Disease Are Labeled By Antisera To The β Amyloid Protein.

Palmert et al. (1989) Proc. Natl. Acad. Sci USA 86:6338–6342. The β–amyloid protein precursor of Alzheimer disease has soluble derivatives found in human brain and cerebrospinal fluid.

Weidemann et al. (1989) Cell 57:115–126. Identification, Biogenesis, and Localization of Precursors of Alzheimer's Disease A4 Amyloid Protein.

Kitaguchi et al. (1988) Nature 331:530–532. Novel precursor of Alzheimer's disease amyloid protein shows protease inhibitory activity.

Ponte et al. (1988) Nature 331:525–527. A new A4 amyloid mRNA contains a domain homologous to serine proteinase inhibitors.

Selkoe et al. (1988) Proc. Natl. Acad. Sci. USA 85:7341. β–Amyloid precursor protein of Alzheimer disease occurs as 110–to 135–kilodalton membrane–associated proteins in neural and nonneural tissues.

Kang et al. (1987) Nature 325:733–736. The precursor of Alzheimer's disease amyloid A4 protein resembles a cell–surface receptor.

Glenner and Wong (1984) Biochem. Biophys. Res. Commun. 120:885–890. Alzheimer's Diseases: Initial Report Of The Purification And Characterization Of A Novel Cerebrovascular Amyloid Protein.

Glenner and Wong (1984) Biochem. Biophys. Res. Commun. 122:1131–1135. Alzheimer's Disease And Down's Syndrome: Sharing Of A Unique Cerebrovascular Amyloid Fibril Protein.

Pulliam et al. (1984) J. Virol. Met. 9:301. Use Of Aggregating Brain Cultures To Study The Replication Of Herpes Simplex Virus Types 1 and 2 In Central Nervous System Tissue.

J.W. Goding (1983) Academic Press (London) pp. 56–75. Monoclonal Antibodies: Principles and Practice.

ANTIBODIES AND FRAGMENTS THEREOF WHICH BIND THE CARBOXYL-TERMINUS OF AN AMINO-TERMINAL FRAGMENT OF βAPP

CROSS-REFERENCE TO RELATED APPLICATION

This application is a divisional of Ser. No. 07/965,971, filed Oct. 26, 1992 now U.S. Pat. No. 5,441,870, which is a continuation-in-part of Ser. No. 07/868,949, filed Apr. 15,1992 now abandoned, the disclosures of which are specifically incorporated herein by reference.

BACKGROUND OF THE INVENTION

1. Field of the Invention

The present invention relates generally to methods and compositions for monitoring the processing of β-amyloid precursor protein. More particularly, the present invention relates to the use of such methods and compositions for the diagnosis, prognosis, and monitoring response to therapy of Alzheimer's disease, and for screening and evaluation of potential drugs for the treatment of Alzheimer's disease.

Alzheimer's disease is characterized by the presence of numerous amyloid plaques and neurofibrillary tangles (highly insoluble protein aggregates) present in the brains of Alzheimer's disease patients, particularly in those regions involved with memory and cognition. While in the past there was significant scientific debate over whether the plaques and tangles are a cause or are merely the result of Alzheimer's disease, recent discoveries indicate that amyloid plaque is a causative precursor or factor. In particular, it has been discovered that the production of β-amyloid peptide, a major constituent of the amyloid plaque, can result from mutations in the gene encoding amyloid precursor protein, a protein which when normally processed will not produce the β-amyloid peptide. The identification of mutations in the amyloid precursor protein gene which cause familial, early onset Alzheimer's disease is the strongest evidence that amyloid metabolism is the central event in the pathogenic process underlying the disease. Four reported disease-causing mutations include with respect to the 770 isoform, valine$^{717}$ to isoleucine (Goate et al. (1991) Nature 349:704–706), valine$^{717}$ to glycine (Chartier Harlan et al. (1991) Nature 353:844–846, valine$^{717}$ to phenylalanine (Murrell et al. (1991) Science 254:97–99) and with respect to the 695 isoform, a double mutation changing lysine$^{595}$-methionine$^{596}$ to asparagine$^{595}$-leucine$^{596}$ (Mullan et al. (1992) Nature Genet 1:345–347). Moreover, β-amyloid peptide is toxic to brain neurons, and neuronal cell death is associated with the disease.

Thus, the ability to monitor cellular processing of the amyloid precursor protein would be of significant value in the diagnosis, prognosis, and therapeutic supervision of Alzheimer's disease. In particular, it would be desirable to identify minimally invasive procedures for screening and evaluating detectable diagnostic markers in readily obtainable patient samples, such as serum, cerebrospinal fluid (CSF), and the like.

A number of potential diagnostic markers for Alzheimer's disease have been proposed. Of particular interest to the present invention are certain fragments of the amyloid precursor protein, including carboxy-terminal fragments (such as the β-amyloid peptide itself and fragments thereof), and amino-terminal fragments (such as certain 25 kD, 105 kD, and 125 kD fragments). As yet, none of the proposed markers has proved to be definitive for the antemortem diagnosis or monitoring of Alzheimer's disease.

Thus, it would be desirable to identify additional and alternative diagnostic markers for Alzheimer's disease. Such markers should be useful by themselves and/or in combination with other diagnostic markers and procedures. Preferably, the diagnostic markers would be detectable in body fluids, such as CSF, blood, plasma, serum, urine, tissue, and the like, so that minimally invasive diagnostic procedures can be utilized.

Of further interest to the present invention are in vitro systems and methods for screening candidate drugs for the ability to inhibit or prevent the production of β-amyloid plaque. It would be desirable to provide methods and systems for screening test compounds for the ability to inhibit or prevent the conversion of amyloid precursor protein to β-amyloid peptide. In particular, it would be desirable to base such methods and systems on metabolic pathways which have been found to be involved in such conversion, where the test compound would be able to interrupt or interfere with the metabolic pathway which leads to conversion. Such methods and systems should be rapid, economical, and suitable for screening large numbers of test compounds.

2. Description of the Background Art

β-amyloid peptide (also referred to as A4, βAP, Aβ, or AβP; see, U.S. Pat. No. 4,666,829 and Glenner and Wong (1984) Biochem. Biophys. Res. Commun. 120:1131–1135) is derived from β-amyloid precursor protein (βAPP), which is expressed in differently spliced forms of 695, 751, and 770 amino acids. See, Kang et al. (1987) Nature 325:773–776; Ponte et al. (1988) Nature 331:525–527; and Kitaguchi et al. (1988) Nature 331:530–532 Normal processing of amyloid precursor protein involves proteolytic cleavage at a site between residues Lys$^{16}$ and Leu$^{17}$ (as numbered for the vAP region where Asp$^{597}$ is residue 1 in Kang et al. (1987)), supra, near the transmembrane domain, resulting in the constitutive secretion of an extracellular domain which retains the remaining portion of the β-amyloid peptide sequence (Esch et al. (1990) Science 248:1122–1124). This pathway appears to be widely conserved among species and present in many cell types. See, Weidemann et al. (1989) Cell 57:115–126 and Oltersdorf et al. (1990) J. Biol. Chem. 265:4492–4497. This normal pathway cleaves within the region of the precursor protein which corresponds to the β-amyloid peptide, thus apparently precluding its formation. Another constitutively secreted form of βAPP has been noted (Robakis et al. Soc. Neurosci. Oct. 26, 1992, Abstract No. 15.5, Anaheim, Calif.) which contains more of the βAP sequence carboxy-terminal to that form described by Esch et al. supra.

Golde et al. (1992) Science 255:728–730, prepared a series of deletion mutants of amyloid precursor protein and observed a single cleavage site within the β-amyloid peptide region. Based on this observation, it was postulated that β-amyloid peptide formation does not involve a secretory pathway. Estus et al. (1992) Science 255:726–728, teaches that the two largest carboxy-terminal proteolytic fragments of amyloid precursor protein found in brain cells contain the entire β-amyloid peptide region.

PCT application WO 92/00521 describes methods for evaluating Alzheimer's disease based on measuring the amounts of certain 25 kD, 105 kD, and 125 kD soluble derivatives of amyloid precursor protein in a patient's cerebrospinal fluid. FIG. 3 of WO 92/00521 suggests that cleavage of amyloid precursor protein may occur adjacent to the amino-terminus of β-amyloid peptide to produce a soluble amino-terminal fragment, but no evidence or discussion of such cleavage is presented in the application. Kennedy et al. (1992) Neurodegeneration 1:59-64, present data for a form of secreted βAPP, which was characterized by its reactivity with antibodies to residues 527-540 of βAPP and the lack of reactivity with antibodies to the first fifteen residues of βAP. No direct evidence is provided to suggest the cleavage site or identity of the carboxy-terminus of the βAPP form. PCT application WO 91/16628 describes methods for diagnosing disease based on detection of amyloid precursor proteins and fragments thereof utilizing antibodies to protease nexin-2 or amyloid precursor protein.

Recent reports show that soluble β-amyloid peptide is produced by healthy cells into culture media (Haass et al. (1992) Nature 359:322–325) and in human and animal CSF (Seubert et al. (1992) Nature 359:325–327).

SUMMARY OF THE INVENTION

Methods and compositions are provided for detecting and monitoring a secreted amino-terminal fragment of β-amyloid precursor protein (βAPP) in biological samples, where the fragment results from cleavage at or near the amino-terminus of the β-amyloid peptide (βAP) region. In particular for the amino acid sequence on βAPP described by Kang et al., supra, (i.e., the "normal" sequence), this truncated secreted fragment of βAPP may be recognized by antibodies raised against peptides comprising certain carboxy-terminal residues of the secreted fragment having an exposed methionine at their carboxy-terminus. Alternatively, naturally occurring or engineered variant sequences of βAPP, such as the double mutation changing lysine$^{595}$-methionine$^{596}$ to asparagine$^{595}$-leucine$^{596}$ reported by Mullan et al. (1992) Nature Genet 1:345-347, can introduce a novel sequence in this region. A binding substance specific for the C-terminal residues of this βAPP sequence would be a preferred means of detection for such sequences.

The secreted fragments will comprise a substantially intact amino-terminal sequence of βAPP terminating within five amino acids of the carboxy-terminal residue (methionine in the case of the normal sequence) which lies adjacent the βAP region in intact βAPP. In particular, the secreted fragments may consist essentially of sequences which terminate in methionine$^{596}$ and lysine$^{595}$ of the 695 amino acid isoform of βAPP, with corresponding numbering for the other isoforms and corresponding amino acids for the mutant βAPP forms, such as, for example, LYS$^{595}$-MET$^{596}$ to ASN$^{595}$-LEU$^{596}$ (the "Swedish" form). The methods and compositions of the present invention are useful both in vivo and in vitro for monitoring intracellular processing of βAPP, particularly for monitoring the cleavage of βAPP to release intact βAP which has been associated with certain diseases, particularly Alzheimer's disease, including the familial form, and Down's syndrome.

In a first particular aspect of the present invention, the secreted amino-terminal fragment of βAPP (ATF-βAPP) is detected by reaction with a binding substance raised against and/or specific for the C-terminal residue of the βAPP sequence that terminates at residue 596 of the 695 isoform of βAPP, typically by reaction with an antibody capable of distinguishing ATF-βAPP from other cleaved forms of βAPP which may be present in a biological sample. Antibodies having the requisite specificity have been raised against synthetic peptide haptens including the C-terminal residues of ATF-βAPP.

In a second particular aspect of the present invention, βAP-related diseases, such as Alzheimer's disease and Down's syndrome, may be diagnosed and monitored in patients based on detection of the ATF-βAPP in patient samples, such as CSF, serum, blood, plasma, urine, tissue, and the like. Elevated ATF-βAPP levels or ratios may be associated with the onset and progression of the disease, and might be reduced with progress in treatment of the disease.

In a third particular aspect, the present invention provides methods for identifying βAP production inhibitors, where an animal is raised or cells are cultured under conditions which result in secretion of ATF-βAPP. The animal or cultured cells are exposed to test compound(s), and test compound(s) which cause a change in the secreted amount or ratios of ATF-βAPP may be identified.

In a fourth particular aspect, the present invention comprises antibody compositions including antibody molecules, such as intact immunoglobulin molecules and immunoglobulin fragments, which are capable of specifically binding to the C-terminus of ATF-βAPP. Such antibody molecules may be prepared in any conventional manner, usually employing an immunogen comprising the C-terminal residues of ATF-βAPP, with for example, the C-terminal methionine being exposed in the normal sequence.

In a fifth particular aspect, the present invention comprises ATF-βAPP in a purified and isolated form. Such compositions will be useful in a variety of conventional assays for the detection of ATF-βAPP. Such compositions may be obtained by isolation and purification of ATF-βAPP from a natural or recombinant source, such as CSF, conditioned media from a suitable cell culture, or the like.

DESCRIPTION OF THE SPECIFIC EMBODIMENTS

The present invention results from the identification of a novel secreted fragment of β-amyloid precursor protein (βAPP) which results from cleavage of an intact β-amyloid peptide (βAP) region from the precursor protein. The novel secreted fragments comprise the amino-terminal portion of βAPP which remains after such cleavage and will be referred to hereinafter as the amino-terminal fragment form of βAPP (ATF-βAPP). ATF-βAPP is believed to be the product of an alternative secretory processing pathway for βAPP, which pathway is present even in normal (non-diseased) cells. It is further believed, however, that the alternate secretory pathway may be responsible for an essential event in the production of βAP in diseased cells in patients, and that abnormal production of ATF-βAPP may be involved in diseases related to βAP plaque, particularly Alzheimer's disease and Down's syndrome. Thus, the present invention provides methods and compositions for monitoring the cellular processing of βAPP based on the detection and measurement of ATF-βAPP in biological samples.

ATF-βAP is identified and recognized by specific binding to antibodies raised against peptides comprising certain residues of βAPP which lie immediately adjacent to the βAP region and for normal βAPP include the carboxy-terminal methionine (numbered as methionine$^{596}$ in the 695 isoform, as set forth below). The peptides will usually include at least five contiguous residues up to and including residue$^{596}$, and specific methods for producing such antibodies are set forth below.

Figure 1A:
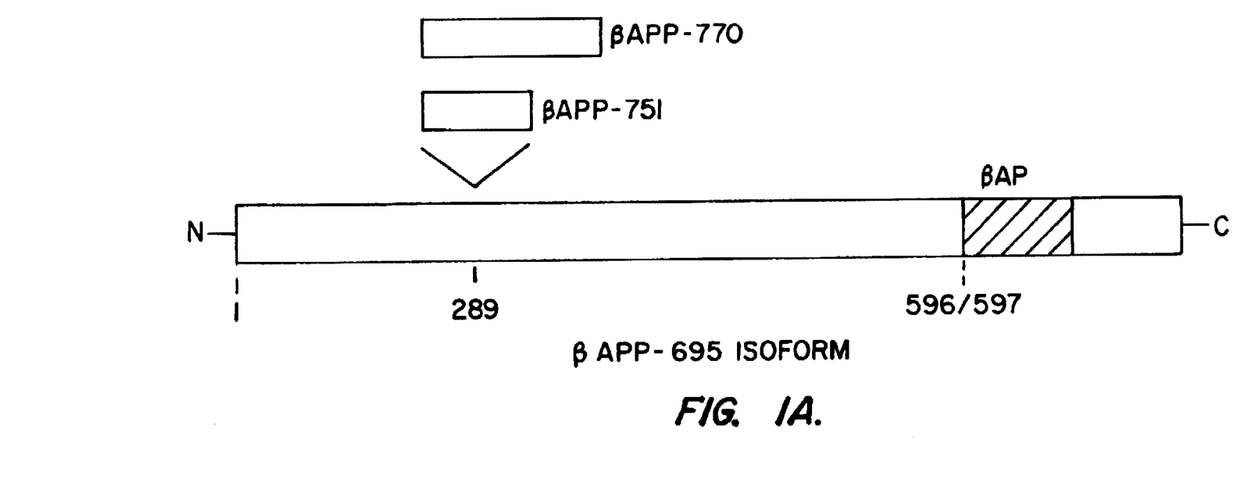
FIGS. 1A and 1B illustrate the various isoforms of normal βAPP and the corresponding isoforms of ATF-βAPP, respectively.
Figure 1B:
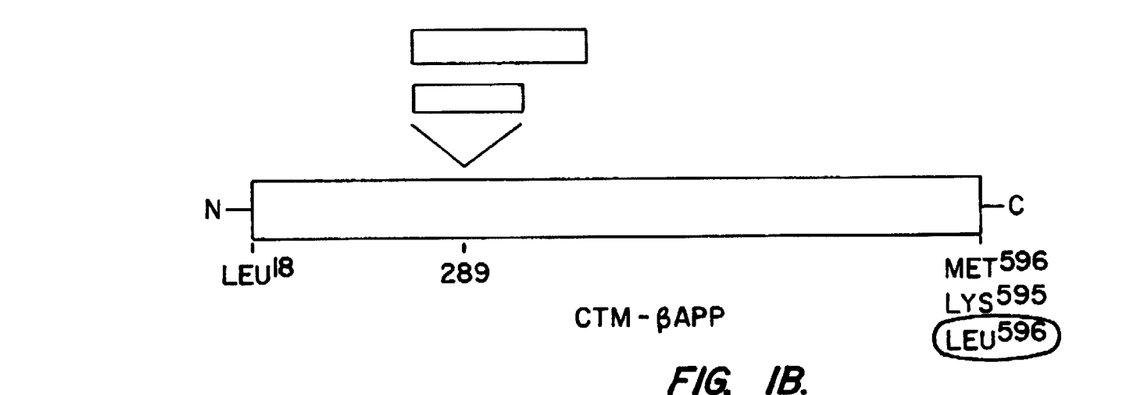

Referring now to FIGS. 1A and 1B, βAPP is found in three isoforms comprising 695, 751, and 770 amino acids, respectively. The 695 isoform is the most common in neuronal cells, with the 751 and 770 isoforms resulting from insertions at residue 289 on the 695 isoform (all numbering of the 695 isoform will be in accordance with Kang et al. (1987) Nature 325:733–736). ATF-βAPP apparently results from proteolytic cleavage of the various βAPP isoforms at or within the five residues on the amino-terminal side of the amino-terminus of the β-amyloid peptide (βAP) region, which is located between residues 596 and 597 of the 695 isoform. Such cleavage results in the exposure of a C-terminal residue, which will usually be methionine$^{596}$, lysine$^{595}$ or leucine$^{596}$, more usually being methionine$^{596}$, shown as MET$^{596}$ and LYS$^{595}$ in FIG. 1B. It will be appreciated, of course, that the C-terminal residues would have a different numbering when the ATF-βAPP is derived from a different βAPP isoform. In particular, the C-terminal methionine would be MET$^{652}$ and MET$^{671}$ and the C-terminal lysine would be LYS$^{651}$ and LYS$^{670}$ in the 751 and 770 βAPP isoforms, respectively. As used hereinafter and in the claims, methionine$^{596}$, lysine$^{595}$, and leucine$^{596}$ will refer generally to corresponding residues in all other isoforms or variants of βAPP. Presently, it is believed that the N-terminal residue of ATF-βAPP is LEU$^{18}$ in all isoforms (based on processing of the amino-terminal end of βAPP in secreted forms which are cleaved within the βAP region).

According to the present invention, ATF-βAPP may be detected and/or measured in a variety of biological samples, including in vitro samples, such as conditioned medium from cultured cells, and in vivo patient samples, typically CSF, blood, serum, plasma, urine, tissue, and the like. Detection and measurement may be accomplished by any technique capable of distinguishing ATF-βAPP from other β-APP fragments which might be found in the sample. Conveniently, immunological detection techniques may be employed which utilize antibodies, antibody fragments, or other equivalent specific binding substances, which bind to a C-terminal residue of ATF-βAPP which is exposed upon cleavage of the βAP region, e.g., methionine$^{596}$, leucine$^{596}$ or lysine$^{595}$. It has been found that such C-terminal-specific antibodies are able to discriminate between the ATF-βAPP and related βAPP fragments. Alternatively, immunological detection techniques may be based on isolated and purified ATF-βAPP using conventional techniques. The preparation of both C-terminal residue-specific antibodies and purified and isolated ATF-βAPP are described hereinafter. Particularly suitable detection techniques include ELISA, Western blotting, radioimmunoassay, and the like.

Other techniques for detecting ATF-βAPP which do not require the use of ATF-βAPP specific antibodies and/or competing antigen may also be employed. For example, two-dimensional gel electrophoresis may be employed to separate closely related soluble fragments of βAPP. Antibodies cross-reactive with many or all of the fragments may then be used to probe the gels, with the presence of ATF-βAPP being identified based on its precise position on the gel. Other techniques for detection of ATF-βAPP are also well within the skill in the art. For example, the secreted βAPP species which contain the amino-terminal region of βAP can be immunologically removed from a sample to isolate ATF-βAPP (see FIG. 2A, lane 2 and FIG. 5, lanes 11 and 12), which can then be detected by any of several methods as discussed above.

Antibodies specific for the ATF-βAPP may be prepared against a suitable antigen or hapten comprising the C-terminal ATF-βAPP sequence including the methionine residue. Conveniently, synthetic peptides may be prepared by conventional solid phase techniques, coupled to a suitable immunogen, and used to prepare antisera or monoclonal antibodies by conventional techniques. One suitable synthetic peptide consists of six residues of ATF-βAPP (ISEVKM) (SEQ ID NO: 3) which are located on the immediate amino-terminal side of βAP and which may be coupled to an immunogen and used to prepare specific antibodies as described in detail in the Experiemtal section. Other suitable peptide haptens will usually comprise at least five contiguous residues within βAPP on the immediate amino-terminal side of βAP, and may include more than six residues (although a peptide including sixteen amino-terminal residues was found to yield antisera which was less specific). The carboxy-terminal 25 residues of the normal ATF-βAPP are as follows (using the single letter amino acid designations).

DRGLT(SEQ ID NO: 7)   TRPGSGLTNI(SEQ ID NO: 8)   KTEEISEVKM(SEQ ID NO: 9)
576                    586                         596

Synthetic polypeptide haptens may be produced by the well-known Merrifield solid-phase synthesis technique where amino acids are sequentially added to a growing chain (Merrifield (1963) J. Am. Chem. Soc. 85:2149–2156). The amino acid sequences may be based on the sequence of ATF-βAPP set forth above or may utilize naturally occurring or engineered mutant sequences. For example, the Swedish mutant would have asparagine$^{595}$-leucine$^{596}$ substituted for lysine$^{595}$-methionine$^{596}$ and another substitution might include only the leucine$^{596}$ substitution for methionine$^{596}$.

Once a sufficient quantity of polypeptide hapten has been obtained, it may be conjugated to a suitable immunogenic carrier, such as serum albumin, keyhole limpet hemocyanin, or other suitable protein carriers, as generally described in Hudson and Hay, *Practical Immunology*, Blackwell Scientific Publications, Oxford, Chapter 1.3, 1980, the disclosure of which is incorporated herein by reference.

Once a sufficient quantity of the immunogen has been obtained, antibodies specific for the C-terminal residue exposed upon cleavage of βAP from ATF-βAPP may be produced by in vitro or in vivo techniques. In vitro techniques involve exposure of lymphocytes to the immunogens, while in vivo techniques require the injection of the immunogens into a suitable vertebrate host. Suitable vertebrate hosts are non-human, including mice, rats, rabbits, sheep, goats, and the like. Immunogens are injected into the animal according to a predetermined schedule, and the animals are periodically bled with successive bleeds having improved titer and specificity. The injections may be made intramuscularly, intraperitoneally, subcutaneously, or the like, and an adjuvant, such as incomplete Freund's adjuvant, will be employed.

If desired, monoclonal antibodies can be obtained by preparing immortalized cell lines capable of producing antibodies having desired specificity. Such immortalized cell lines may be produced in a variety of ways. Conveniently, a small vertebrate, such as a mouse is hyperimmunized with the desired immunogen by the method just described. The vertebrate is then killed, usually several days after the final immunization, the spleen cells removed, and the spleen cells immortalized. The manner of immortalization is not critical. Presently, the most common technique is fusion with a myeloma cell fusion partner, as first described by Kohler and Milstein (1975) Nature 256:495–497. Other techniques including EBV transformation, transformation with bare DNA, e.g., oncogenes, retroviruses, etc., or any other method which provides for stable maintenance of the cell line and production of monoclonal antibodies. Specific techniques for preparing monoclonal antibodies are described in *Antibodies: A Laboratory Manual*, Harlow and Lane, eds., Cold Spring Harbor Laboratory, 1988, the full disclosure of which is incorporated herein by reference.

In addition to monoclonal antibodies and polyclonal antibodies (antisera), the detection techniques of the present invention will also be able to use antibody fragments, such as F(ab), Fv, $V_L$, $V_H$, and other fragments. It will also be possible to employ recombinantly produced antibodies (immunoglobulins) and variations thereof as now well described in the patent and scientific literature. See, for example, EPO 8430268.0; EPO 85102665.8; EPO 85305604.2; PCT/GB 85/00392; EPO 85115311.4; PCT/US86/002269; and Japanese application 85239543, the disclosures of which are incorporated herein by reference. It would also be possible to prepare other recombinant proteins which would mimic the binding specificity of antibodies prepared as just described.

The present invention further comprises isolated and purified ATF-βAPP, usually obtained in substantially pure form. "Substantially pure" means at least about 50% w/w (weight/weight) or more purity with substantial freedom from interfering proteins and contaminants. Preferably, the ATF-βAPP will be isolated or synthesized in a purity greater than 50% w/w, preferably being 80% w/w or higher. The ATF-βAPP may be purified from a natural source by conventional protein purification techniques, with homogeneous compositions of at least about 50% w/w purity being purified by use of antibodies prepared as described above using conventional immunoaffinity separation techniques. Suitable natural starting materials include conditioned medium from ATF-βAPP-producing cell lines, such as fetal brain cell cultures, and the like. Alternatively, the ATF-βAPP may be isolated from biological samples obtained from a human host, such as CSF, serum, and the like. Suitable protein purification techniques are described in *Methods in Enzymology*, Vol. 182, Deutcher, ed., Academic Press, Inc., San Diego, 1990, the disclosure of which is incorporated herein by reference.

Antibodies and purified ATF-βAPP prepared as described above can be used in various conventional immunological techniques for detecting ATF-βAPP in biological samples, particularly in vivo patient samples for the monitoring of β-amyloid-related diseases and in conditioned media from cell culture for monitoring the intracellular processing of βAPP. Suitable immunological techniques include immunoassays, such as ELISA, Western Blot analyses, and the like. Numerous specific immunological detection techniques are described in Harlow and Lane, supra.

Detection of ATF-βAPP in patient samples can be used for diagnosing and monitoring of Alzheimer's disease and other diseases related to β-amyloid plaque deposition, such as Down's syndrome. Suitable patient samples include CSF, blood, serum, plasma, urine, tissue, and the like. Presence of the disease will generally be associated with elevated levels of ATF-βAPP, or elevated ratios of the amount of ATF-βAPP to the amounts of other secreted βAPP fragments (i.e., those βAPP fragments cleaved within or carboxy terminal to the βAP region) when compared to those values in normal individuals, i.e., individuals not suffering from Alzheimer's disease or other β-amyloid-related disease. The amount of ATF-βAPP may be compared to the amount of another species of APP, either an isoform (e.g., 695, 751 or 770) and/or a form further defined by its carboxy-terminus (e.g., forms cut at and/or carboxy-terminal to that site described by Esch et al.). In addition to initial diagnostic procedures, levels of ATF-βAPP may be monitored in order to follow the progress of the disease, and potentially follow the effectiveness of treatment. It would be expected that levels of ATF-βAPP would decrease with an effective treatment regimen.

In vitro monitoring of ATF-βAPP levels in cultured medium from a suitable cell culture may be used for drug screening. By growing cells under conditions which result in the secretion of ATF-βAPP into the culture medium, and exposing the cells to test compounds, the effect of these test compounds on ATF-βAPP secretion may be observed. It would be expected that test compounds which are able to diminish the amount of ATF-βAPP would be candidates for testing as inhibitors of βAP formation. Suitable cell lines include human and animal cell lines, such as 293 human kidney cell line, human neuroglioma cell lines, human HeLa cells, primary endothelial cells (e.g., HUVEC cells), primary human fibroblasts or lymphoblasts (including endogenous cells derived from patients with βAPP mutations), primary human mixed brain cells (including neurons, astrocytes and neuroglia), Chinese hamster ovary (CHO) cells, and the like. Cell lines which preferentially increase the levels or ratios of ATF-βAPP would be particularly useful in the methods of invention.

Similarly, in vitro monitoring of ATF-βAPP in animal models of Alzheimer's disease, such as the mouse model disclosed in WO 91/19810, the disclosure of which is incorporated herein by reference, may also be used to screen test compounds for therapeutic effectiveness (usually for testing of compounds which have previously been identified by an in vitro screen). The test compound(s) are administered to the animal and the level of ATF-βAPP or ratio of ATF-βAPP to other βAPP fragments observed. Those compounds which reduce the level of ATF-βAPP, or decrease the ratio of ATF-βAPP to other βAPP fragments, will be considered to be candidates for further evaluation.

The test compounds can be any molecule, compound, or other substance which can be added to the cell culture without substantially interfering with cell viability. Suitable test compounds may be small molecules, biological polymers, such as polypeptides, polysaccharides, polynucleotides, and the like. The test compounds will typically be administered to the culture medium at a concentration in the range from about 1 nM to 1 mM, usually from about 10 µM to 1 mM.

Test compounds which are able to inhibit secretion of ATF-βAPP are considered as candidates for further determinations of the ability to block β-amyloid production in pathogenic cells. Inhibition of secretion indicates that cleavage of βAPP at the amino-terminus of βAP has likely been at least partly blocked, reducing the amount of a processing intermediate available for conversion to β-amyloid peptide.

The present invention further comprises methods for inhibiting β-amyloid production in cells, where the method includes administering to the cells compounds selected by the method described above. The compounds may be added to cell culture in order to inhibit βAP production by the cultured cells. The compounds may also be administered to a patient in order to inhibit the deposition of amyloid plaque associated with Alzheimer's and other βAP-related diseases.

The present invention further comprises pharmaceutical compositions incorporating a compound selected by the above-described method and including in a pharmaceutically acceptable carrier. Such pharmaceutical compositions should contain a therapeutic or prophylactic amount of at least one compound identified by the method of the present invention. The pharmaceutically acceptable carrier can be any compatible, non-toxic substance suitable to deliver the compounds to an intended host. Sterile water, alcohol, fats, waxes, and inert solids may be used as the carrier. Pharmaceutically acceptable adjuvants, buffering agents, dispersing agents, and the like may also be incorporated into the pharmaceutical compositions. Preparation of pharmaceutical conditions incorporating active agents is well described in the medical and scientific literature. See, for example, Remington's Pharmaceutical Sciences, Mack Publishing Company, Easton, Pa., 16th Ed., 1982, the disclosure of which is incorporated herein by reference.

The pharmaceutical compositions just described are suitable for systemic administration to the host, including both parenteral, topical, and oral administration. The pharmaceutical compositions may be administered parenterally, i.e. subcutaneously, intramuscularly, or intravenously. Thus, the present invention provides compositions for administration to a host, where the compositions comprise a pharmaceutically acceptable solution of the identified compound in an acceptable carrier, as described above.

Frequently, it will be desirable or necessary to introduce the pharmaceutical compositions directly or indirectly to the brain. Direct techniques usually involve placement of a drug delivery catheter into the host's ventricular system to bypass the blood-brain barrier. Indirect techniques, which are generally preferred, involve formulating the compositions to provide for drug latentiation by the conversion of hydrophilic drugs into lipid-soluble drugs. Latentiation is generally achieved through blocking of the hydroxyl, carboxyl, and primary amine groups present on the drug to render the drug more lipid-soluble and amenable to transportation across the blood-brain barrier. Alternatively, the delivery of hydrophilic drugs can be enhanced by intra-arterial infusion of hypertonic solutions which can transiently open the blood-brain barrier.

The concentration of the compound in the pharmaceutical carrier may vary widely, i.e. from less than about 0.1% by weight of the pharmaceutical composition to about 20% by weight, or greater. Typical pharmaceutical composition for intramuscular injection would be made up to contain, for example, one to four ml of sterile buffered water and one µg to one mg of the compound identified by the method of the present invention. The typical composition for intravenous infusion could be made up to contain 100 to 500 ml of sterile Ringer's solution and about 1 to 100 mg of the compound.

The pharmaceutical compositions of the present invention can be administered for prophylactic and/or therapeutic treatment of diseases related to the deposition of βAP, such as Alzheimer's disease and Down's syndrome. In therapeutic applications, the pharmaceutical compositions are administered to a host already suffering from the disease. The pharmaceutical compositions will be administered in an amount sufficient to inhibit further deposition of βAP plaque. An amount adequate to accomplish this is defined as a "therapeutically effective dose." Such effective dose will depend on the extent of the disease, the size of the host, and the like, but will generally range from about 0.01 µg to 10 mg of the compound per kilogram of body weight of the host, with dosages of 0.1 µg to 1 mg/kg being more commonly employed.

For prophylactic applications, the pharmaceutical compositions of the present invention are administered to a host susceptible to the βAP disease, but not already suffering from such disease. Such hosts may be identified by genetic screening and clinical analysis, as described in the medical literature. The pharmaceutical compositions will be able to inhibit or prevent deposition of the βAP plaque at a very early stage, preferably preventing even the initial stages of the β-amyloid disease. The amount of the compound required for such prophylactic treatment, referred to as a prophylactically-effective dosage, are generally the same as described above for therapeutic treatment.

The following examples are offered by way of illustration, not by way of limitation.

EXPERIMENTAL

Materials and Methods

1. Antibody and Affinity Matrix Preparation

Monoclonal antibody 6C6 was raised and screened in the same manner as antibody 10D5 (Hyman et al. (1992) J. Neuropath. Exp. Neurol. 51:76) using a synthetic peptide containing βAP residues 1–28 conjugated to rabbit serum albumin as the immunogen. Both 10D5 and 6C6 recognize an epitope within the first 16 amino acids of the βAP sequence. 6C6 was more efficient than 10D5 in immunoprecipitation and was used as a capture antibody. To prepare 6C6 resin, 4 mls of Affigel® 10 (Bio-Rad Laboratories, Hercules, Calif.) was washed with cold water and combined with 3 mls of 6C6 (12.5 mg/ml in PBS (2.7 mM KCl, 1.5 mM $KH_2PO_4$, 8.1 mM $Na_2HPO_4$, 137 mM NaCl, pH 7.5) 0.5 M NaCl. The coupling proceeded overnight at 4° C. with gentle shaking. 400 µl of 1M Tris, pH 8.0, was then added, and shaking was continued for 40 minutes. The resin was then washed with TTBS (137 mM NaCl, 5 mM KCl, 25 mM Tris, 0.5% Tween® 20, pH 7.5) exhaustively before use. Antibody 7H5 is also described in Hyman et al. (1992), supra.

Antibodies (designated antibody 92) were raised against a synthetic peptide including residues 591–596 of βAPP (as numbered in Kang et al. (1987), supra). The peptide (N-acetyl-CISEVKM) (SEQ ID NO: 5) was conjugated to rabbit serum albumin which had been activated with sulfo-maleimido benzoyl-N-hydroxysuccinimide ester to form an immunogen. Antisera were raised against the immunogen in rabbits by standard methodologies. During each inoculation, rabbits received 5µg of immunogen in 0.1 ml injections subcutaneously at approximately 10 sites (50 µg/boost). The same peptide was coupled to Sulfo-link™ gel (Pierce Chemical Co., Rockford, Ill.) for the affinity purification of antibodies from the IgG fraction.

A more detailed description of the antibody 92 preparation is as follows. Rabbit serum albumin (12.3 mg) was incubated with 13 mg of sulfo-maleimido benzoyl-N-hydroxysuccinimide ester in 1.25 mls of 0.05 M $KH_2PO_4$, pH 7.0 for 20 minutes at 0° C. The mixture was then immediately subjected to gel filtration on a 1 × 75 cm column of Sephadex G-10 equilibrated with the phosphate buffer. The protein eluant in the excluded volume was pooled and immediately combined with 30 mg of N-acetyl-CISEVKM (SEQ ID NO: 5) peptide which was synthesized by standard automated solid phase methodologies. The coupling reaction (20 ml volume) was allowed to proceed overnight and was then sent to a commercial facility for antibody generation. The injection protocol was to emulsify the antigen in an equal volume of Freund's complete adjuvant and subcutaneously inject a total of 50 µg of antigen in 0.1 ml aliquots in approximately 10 sites. Every three weeks thereafter, a booster injection was given by an identical protocol except Freund's incomplete adjuvant was used as the emulsifier. Rabbits were bled one week following each injection and the serum examined for titer by reaction to peptide in ELISA. The IgG was purified from the positive reacting sera by precipitation with 50% $(NH_4)_2SO_4$, (2 x's) and dialyzed against PBS. The N-acetyl-CISEVKM (SEQ ID NO: 5) peptide was conjugated to Sulfo-link™ gel (Pierce Chemical Co., Rockford, Ill.) using the manufacturer's recommendations to generate an affinity resin to purify the peptide specific antibodies. The IgG fraction was applied to the column and, after washing through non-specifically bound material with PBS, the antibodies were eluted with 0.1M glycine pH 2.5 0.5M NaCl and then dialyzed vs PBS before freezing.

2. Human Fetal Brain Cell Culture

Fetal neural tissue specimens were obtained from 12–14 week old fetal cadavers. Samples of cerebral cortex were rinsed twice with Hank's Balanced Saline Solution (HBSS). Cortical tissue (2–3 grams) was placed in 10 mls of cold HBSS to which 1 mg of DNase (Sigma Chemical Co., St. Louis, Mo. D3427) was added. The triturated suspension was filtered through Nitex nylon screens of 210 µm then 130 µm, as described by Pulliam et al. (1984) J. Virol. Met. 9:301.

Cells were harvested by centrifugation and resuspended in neuronal medium (MEM fortified with 10% fetal bovine serum, 1% glucose, 1 mM NaPyruate, 1 mM glutamine, 20 mM KCl). Polyethyleneimine coated 100 mm dishes were seeded with $1.5 \times 10^7$ cells in 8 mls of neuronal medium. The medium was exchanged twice weekly. All cultures in this study were grown in vitro at least 30 days. For serum-free growth conditions, cultures were shifted into defined medium (DMEM supplemented with 5 µg/ml bovine insulin; 0.1 mg/ml human transferrin; 0.1 mg/ml BSA fraction V; 0.062 µg/ml progesterone, 1.6 µg/ml putrescine; 0.039 µg/ml sodium selenite, 0.042 µg/ml thyroxine; and 0.033 µg/ml triiodo-L-thyronine), and after 3 days the supernantant was harvested.

Conditioned medium from the cells (10 ml) was harvested. EDTA (5 mM), leupeptin (10 µg/ml), and Tris-HCl (20 mM, pH 8.0) were added to each 10 ml sample at the indicated final concentration, and the sample spun 30,000 xg for 20 minutes at 4° C. The resulting supernatant was divided into two equal aliquots, 6C6 resin was added to one of the aliquots (200 µl of resin with approximately 5 mg/ml 6C6 bound). Both aliquots were gently mixed for 6 hours at 4° C., the resin was pelleted, and a second 200 µl aliquot of resin was added. The samples were further mixed overnight at 4° C. The combined resins were washed twice with TTBS, then briefly extracted twice with one ml aliquots of 0.1M glycine, 0.1M NaCl, pH 2.8.

The material extracted from the resin, the medium depleted by the resin, and the starting medium were individually precipitated with 10% TCA (trichloro-acetic acid) at 0° C. for one hour, the pellets washed with acetone and then resuspended in 150 µl of SDS-PAGE sample buffer under reducing conditions and boiled. Each sample (25 µl) was subjected to SDS-PAGE using 10–20% tricine gels (Novex). The proteins were transferred to ProBlot PVDF membranes overnight at 40 V. Visualization of immunoreactive proteins employed the TROPIX chemiluminescence system according to the manufacturer's directions for the AMPPD substrate. Primary antibody concentrations used were: anti-5, 0.1 µg/ml; 92, 2 µg/ml; 10D5, 2 µg/ml.

3. Culture of Human 293 Cells

Human 293 cells (ATCC No. CRL-1573) were modified to overexpress APP (Selkoe et al. (1988) Proc. Natl. Acad. Sci. USA 85:7341). Cells were grown in 10 cm dishes to subconfluency prior to use. Metabolic labelling and immunoprecipitation were performed essentially as previously described in Oltersdorf et al. (1989) Nature 341:144 and (1990) J. Biol. Chem. 265:4492. In brief, labelling was performed in 10 cm dishes. Cells were washed in methionine-free medium, incubated for 20 minutes in 2 ml methionine-free medium supplemented with 0.5 mCi $^{35}S$-methionine, washed in full medium, and chased for 2 hours in 3 ml of full medium. Conditioned medium was collected and cleared at 3000 xg for 10 minutes followed by preabsorption with protein A Sepharose® (Pharmacia, Piscataway, N.J.). Immunoprecipitation was performed with 1.5 mg protein A Sepharose® per sample. Antibody anti-5 was used at 2 μg per sample; 6C6, 7H5 and 92 were used at 10 μg per sample. 5 mg of rabbit anti mouse IgG were used with 6C6 and 7H5 as well as in the control samples. Precipitates were washed four times in TBS (137 mM NaCl, 5 mM KCl, 25 mM Tris, pH 7.5), 0.1% NP40, 5 mM EDTA, 1 mM PMSF, 10 μg/ml leupeptin. SDS-PAGE was performed on 5% Laemmli gels.

4. Culture of Human 293 Cells Transfected with Swedish Mutation.

Duplicate wells in a 6 well tray of human kidney 293 cells were transiently transfected with plasmid vectors expressing either normal human βAPP or the Swedish mutation variant βAPP using DOTAP mediated transfection as described by the manufacturer (Boehringer Mannheim). 40 hours later the cells were placed into methionine free DME containing 10% fetal calf serum and 20 minutes later they were labeled for 35 minutes with 200 μCi/ml $^{35}$S-methionine. The cells were then placed back into normal DME medium containing 10% fetal calf serum and incubated another 2.5 hours. The medium was collected from the cells, and spun at 1000 ×g for 15 minutes to remove all the cells. The supernatants were split in half and half was immunoprecipitated with anti-5 antibody by standard methods. The other half was incubated overnight with agarose-coupled 6C6 antibody, and the material bound to the 6C6 agarose was separated by centrifugation. The remaining material was then immunoprecipitated with anti-5 antibody. The total anti-5 immunoprecipitates (α5+), 6C6 bound precipitates (6C6+) and 6C6 nonreactive, anti-5 reactive immunoprecipitates (6C6–,α5+) were run on a 5% Laemmli gel and immunoreactive proteins were visualized by autoradiography.

DESCRIPTION OF THE EXPERIMENTAL FIGURES

Figure 2A:
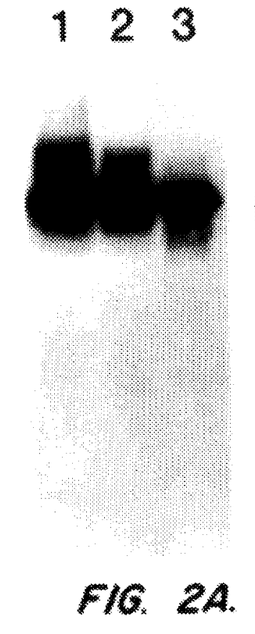
FIGS. 2A, 2B, and 2C, are chemiluminescent gel patterns of material derived from conditioned medium of a human fetal brain cell culture. Lanes 1, 2, and 3 of each gel represent the untreated conditioned medium, the conditioned medium depleted by reaction with antibody which recognizes an epitope within the β-amyloid peptide residues 1–16, and the material removed by this antibody, respectively. Panels A, B, and C represent the following probes: anti-5 antibody (which recognizes locations on βAPP amino-terminal to β-amyloid peptide region), antibody 92 (which was raised against a synthetic peptide terminating in the C-terminal methionine exposed by cleavage of βAP from βAPP), and antibody 10D5 (a monoclonal antibody which recognizes an epitope of βAP within residues 1–16), respectively.
Figure 2B:
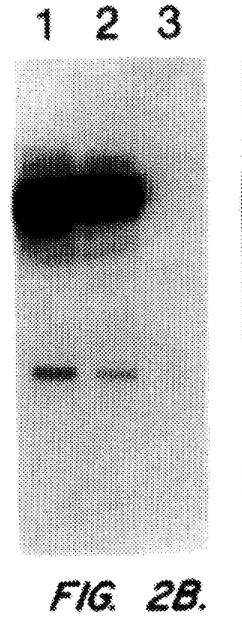
Figure 2C:
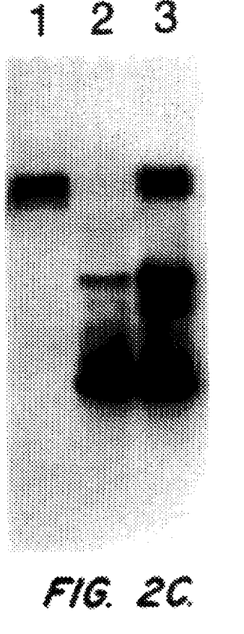

FIG. 2: Demonstration of truncated βAPP in conditioned medium from human mixed-brain cell cultures.

Sample 1 is the conditioned-medium from culture; sample 2 is the medium depleted of 6C6-reactive βAPP; and sample 3 is the material extracted from the 6C6 resin. Panel A was probed with anti-5 antibodies which were raised against the βAPP sequence 444–592 (Oltersdorf et al. (1989) supra, and (1990) supra. Panel B was probed with antibody 92, described in the Materials and Methods section. Panel C was probed with 10D5, a monoclonal antibody which recognizes an epitope within βAP residues 1–16, as described in the Materials and Methods section. The lower molecular weight bands observed in C2 and C3 were not seen in C1 and are derived from the 6C6 resin and are recognized by goat-antimouse IgG alkaline phosphatase conjugate independent of a primary antibody (data not shown).

Figure 3:
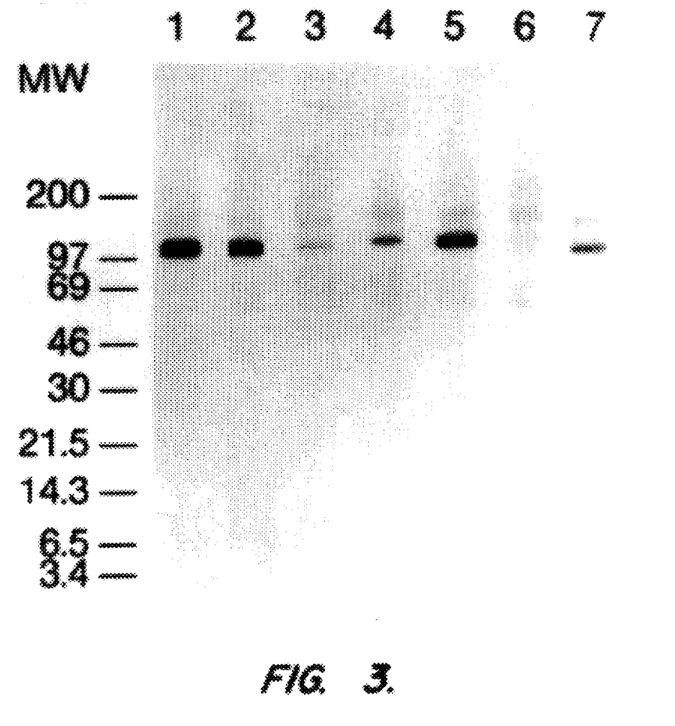
FIG. 3 is a chemiluminescent gel pattern obtained by examining human lumbar CSF. The CSF was probed with 92 antibody either alone (lane 1) or preincubated with various peptides representing variations of the C-terminus of ATF-βAPP. A significant competition (reduction in binding) was observed with peptides terminating in the C-terminal methionine (lanes 3, 4, 6, and 7). The peptides were as follows: Lane 1, no competing peptide added; Lane 2, GSGLTNIKTEEISEVK (SEQ ID NO: 1); Lane 3, YSGLTNIKTEEISEVKM (SEQ ID NO: 2); Lane 4, ISEVKM (SEQ ID NO: 3); Lane 5, EISEVKMD (SEQ ID NO: 4); Lane 6, CISEVKM (SEQ ID NO: 5); Lane 7, YISEVKM (SEQ ID NO: 6). MW = molecular mass markers (indicated in kilodaltons).

FIG. 3: Specificity of the 92 Antibody

One milliliter of a human lumbar CSF specimen obtained from a 75 year old male was precipitated with 10% TCA to effect a ten-fold concentration and processed as described in FIG. 2, except that the gel well was a 4 cm slot. The 92 antibody was diluted to 6.7 μg/ml in 0.5 mls of TTBS in the presence of various potentially competing peptides, each at an approximate concentration of 60 μM, for 10 hours at 4° C. with gentle mixing. The antibody was then diluted eight-fold in 1% gelatin/TTBS before incubation with strips of the blot of CSF-derived material and processed as described in FIG. 2. The competing peptides were as follows: Lane 1, no competing peptide added; Lane 2, GSGLT-NIKTEEISEVK (SEQ ID NO: 1); Lane 3, YSGLTNIK-TEEISEVKM (SEQ ID NO: 2); Lane 4, ISEVKM (SEQ ID NO: 3); Lane 5, EISEVKMD (SEQ ID NO: 4); Lane 6, CISEVKM (SEQ ID NO: 5); Lane 7, YISEVKM (SEQ ID NO: 6). MW = molecular mass markers (indicated in kilodaltons).

Figure 4:
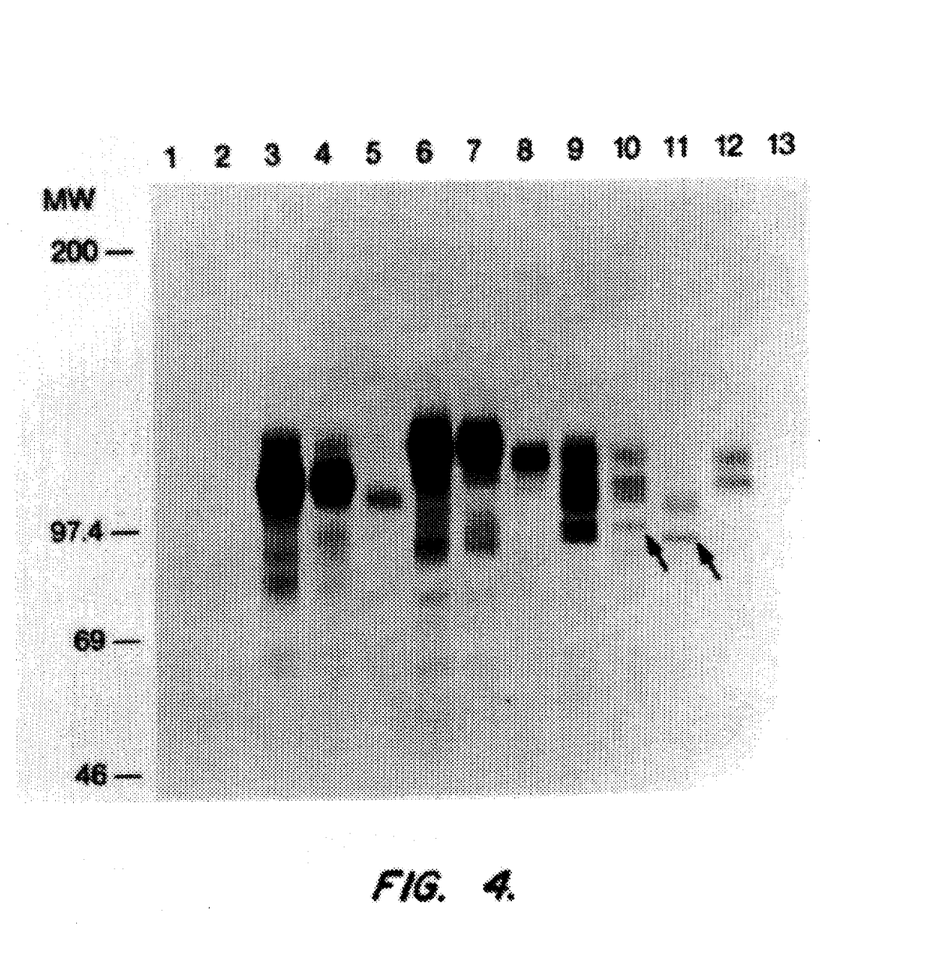
FIG. 4 is an autoradiogram representing electrophoretic gel patterns obtained by immunoprecipitation of conditioned medium from various cell lines. The material secreted by human fetal brain cultures and immunoprecipitated by antibody 92 (lane 11 at the arrow) is apparently smaller than the material precipitated by antibody 6C6 (lane 10 at the arrow). Antibody 6C6 recognizes an epitope within residues 1–16 of βAP.

FIG. 4: Molecular mass heterogeneity of secreted forms of APP in immunoprecipitation detected by antibodies against different C-termini in cell lines and primary human fetal brain cultures.

Antibodies: anti-5: Lanes 3, 6, 9; 6C6 (directed against βAP peptide residues 1–16): Lanes 4, 7, 10; antibody 92 (against APP amino acids 591 to 596): Lanes 5, 8, 11; 7H5 (against APP-KPI): Lane 12. Cells: left panel (lanes 1 and 3–5): 293 cells stably transfected with APP 695; middle panel (lanes 2 and 6–8): 293 cells stably transfected with APP 751; right panel (lanes 9–13): human fetal brain cultures. Controls: lanes 1, 2, and 13: rabbit anti mouse IgG antibody. Arrows: an example of molecular mass difference between secreted forms of APP recognized by antibodies 6C6 and 92. SDS-PAGE was performed on a 5% Laemmli gel. MW = molecular mass markers (indicated in kilodaltons).

Figure 5:
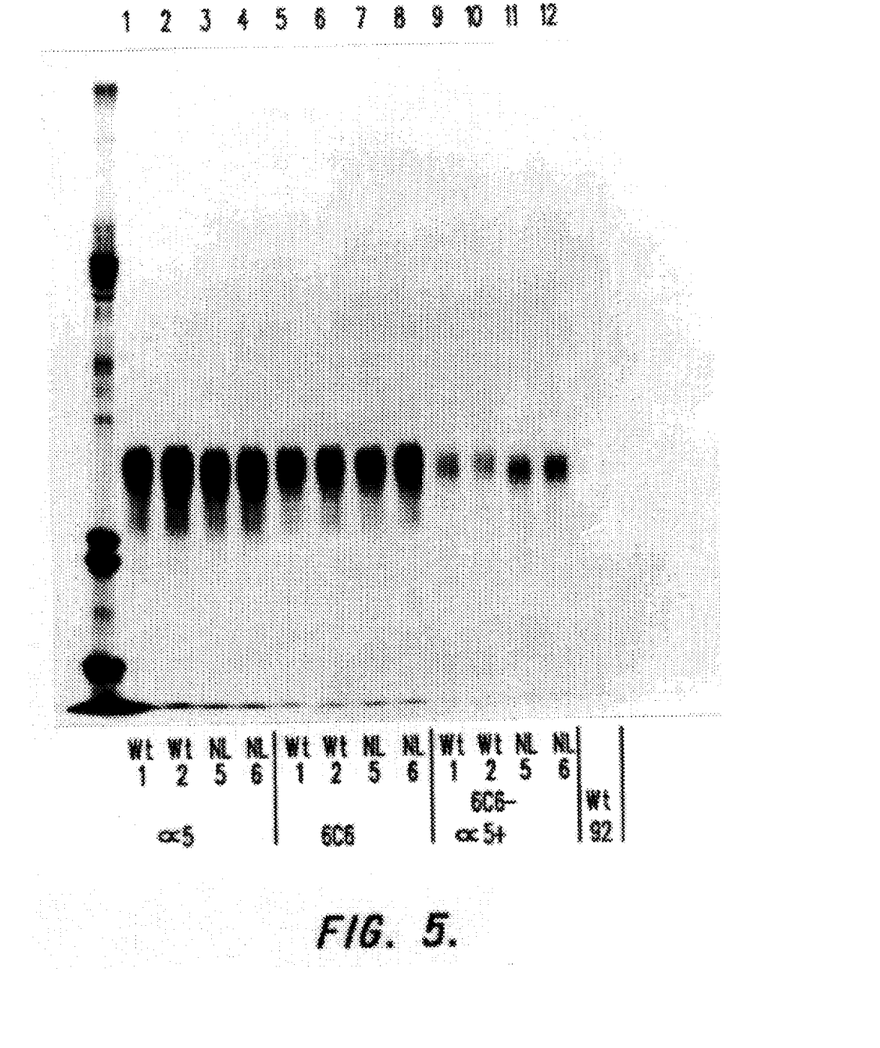
FIG. 5 is an autoradiogram representing electrophoretic gel patterns obtained by immunoprecipitation of conditioned medium from human 293 cell lines transfected with cDNA encoding both normal and Swedish βAPP. The amount of AFT-βAPP material secreted by the Swedish transfected cells (lanes 11 and 12) is qualitatively greater than that produced by normal βAPP transfectants (lanes 9 and 10).

FIG. 5: Demonstration of truncated βAPP in conditioned medium from human 293 cells transfected with Swedish mutation.

FIG. 5 shows results from duplicate transfections for both normal and Swedish forms. Lanes 1–4 are α5+; lanes 5–8 are 6C6+; and lanes 9–12 are 6C6–, α5+ samples. Lanes 1, 2, 5, 6, 9 and 10 are from normal βAPP, lanes 3, 4, 7, 8, 11 and 12 are from Swedish βAPP. The Swedish mutation results in the production of increased AFT-βAPP as lanes 11 and 12 contain more ATF-βAPP material than lanes 9 and 10.

RESULTS

Monoclonal antibody 6C6 which recognizes an epitope of βAP within residues 1–16 was used to immuno-deplete certain βAPP fragments from various samples. The monoclonal antibody 6C6 was coupled to resin (as described above) and incubated with the conditioned medium from human fetal brain cell cultures as described above. As can be seen (FIG. 2, lane C2), this resin effectively removes the βAPP containing βAP 1–16 from the conditioned medium of the cell culture. Substantial βAPP immunoreactivity, however, is not captured by the resin as detected by anti-5 antibody directed against an epitope N-terminal to the βAP region (FIG. 2, lane A2).

In order to characterize this apparently novel form of βAPP, we raised antibodies against a synthetic peptide which included βAPP residues 591–596 (as described above). This antibody (designated 92) was found to recognize the species of βAPP not captured by the resin, (FIG. 2, lane B2) but surprisingly did not react with the secreted form of βAPP containing the βAP 1–16 sequence (lane B3).

The explanation for this lack of cross reactivity appears to be that the 92 antibody recognizes an epitope in βAPP including the carboxy-terminal methionine, corresponding to residue 596. Accordingly, we examined the ability of various synthetic peptides to block the immunoreactivity generated with 92. As can be seen in FIG. 3, βAPP sequence-based peptides ending with the equivalent of methionine 596 substantially block the reaction of 92, while peptides one amino acid longer or shorter at their carboxy-termini are comparatively ineffective in competition. The same pattern of peptide competition was observed in cell culture supernatants (data not shown) and in CSF. A series of pulse-chase experiments revealed that detectable amounts of antibody 92 immunoprecipitable material are produced by 293 cells overexpressing either the 695 or 751 isoforms of βAPP (FIG. 4, lanes 5 and 8). Similar experiments on human fetal brain cell cultures show that 92 immunoprecipitable material can be resolved from 6C6 reactive βAPP by low percentage (5%) SDS-PAGE (FIG. 4, lanes 9–11). In the fetal brain cell cultures, the alternative processing of Kunitz protease inhibitory domain (KPI)-containing βAPP forms is less apparent, although faint co-migrating bands are observed with antibody 92 and anti-KPI antibody 7H5 immunoprecipitations (lanes 11, 12).

The ability to resolve the antibody 92 and 6C6 precipitable materials in mixed brain cultures is due, at least in part, to the nearly equal amounts of the respective forms produced as compared to the situation in 293 cells. Estus et al. (1992), supra, observed that compared with other tissues, human brain contained a relatively higher amount of the potentially amyloidogenic carboxy-terminal fragment that, based upon size, appears to begin at or near the amino-terminus of βAP.

The temporal coincidence of the appearance of antibody 92 and 6C6 precipitable βAPP materials argues against the likelihood of a second proteolytic event occurring post-secretion, particularly since longer chase times do not result in a noticeable alteration in the ratio of the 92 and 6C6 reactive species (data not shown). The resolution of the secreted forms by SDS-PAGE, coupled with the complete lack of immunological cross-reactivity of these species, further demonstrate the existence of an alternative secretory pathway. The alternative cleavage site was designated as the β-secretase site to emphasize that cleavage occurs amino-terminal to the βAP as distinct from the cleavage described by Esch et al. (1990) supra which occurs within the βAP.

Although the foregoing invention has been described in detail for purposes of clarity of understanding, it will be obvious that certain modifications may be practiced within the scope of the appended claims.

What is claimed is:

1. An antibody composition comprising antibody molecules that specifically recognize an amino-terminal fragment of βAPP which is cleaved at the amino-terminus of β-amyloid peptide, but which antibody molecules do not specifically recognize a secreted fragment of βAPP whose sequence extends into the sequence of β-amyloid peptide.

2. The antibody composition of claim 1, wherein the antibody molecules comprise intact immunoglobulins.

3. The antibody composition of claim 1, wherein the antibody molecules comprise immunoglobulin fragments which specifically recognize the amino-terminal fragment of βAPP which is cleaved at the amino-terminus of β-amyloid peptide, but which do not specifically recognize a secreted fragment of βAPP whose sequence extends into the sequence of β-amyloid peptide.

4. The antibody composition of claim 3 wherein the immunoglobulin fragment is an F(ab) fragment, and Fv fragment, a $V_L$ fragment or a $V_H$ fragment.

5. The antibody composition of claim 1, wherein the antibody molecules have been raised against a peptide comprising at least residues 591–596 of βAPP.

6. The antibody composition of claim 5, comprising antisera raised against said peptide.

7. The antibody composition of claim 1, wherein the amino-terminal fragment of βAPP has a carboxy-terminal residue that corresponds to methionine$^{596}$ or leucine$^{596}$.

8. The antibody composition of claim 1 wherein the antibody molecules are labelled.

9. The antibody composition of claim 1 comprising monoclonal antibodies.

10. The antibody composition of claim 9 wherein the antibody molecules are labelled.

11. The antibody composition of claim 1 wherein the antibody molecules are mouse antibody molecules, rabbit antibody molecules, sheep antibody molecules or goat antibody molecules.

12. The antibody composition of claim 1 wherein the antibody molecules are recombinantly produced.

13. A hybridoma that produces antibody molecules that specifically recognize an amino-terminal fragment of βAPP which is cleaved at the amino-terminus of β-amyloid peptide, but which antibody molecules do not specifically recognize a secreted fragment of βAPP whose sequence extends into the sequence of β-amyloid peptide.

14. The hybridoma of claim 13 wherein the amino-terminal fragment of βAPP has a carboxy-terminal residue that corresponds to methionine$^{596}$ or leucine$^{596}$.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

Gly Ser Gly Leu Thr Asn Ile Lys Thr Glu Glu Ile Ser Glu Val Lys
    1             5                    10                 15

( 2 ) INFORMATION FOR SEQ ID NO:2:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:2:

Tyr Ser Gly Leu Thr Asn Ile Lys Thr Glu Glu Ile Ser Glu Val Lys
    1             5                    10                 15
    Met ( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:3:

Ile Ser Glu Val Lys Met
    1             5

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:4:

```
Glu  Ile  Ser  Glu  Val  Lys  Met  Asp
 1                  5
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:5:

```
Cys  Ile  Ser  Glu  Val  Lys  Met
 1                  5
```

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:6:

```
Tyr  Ile  Ser  Glu  Val  Lys  Met
 1                  5
```

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:7:

```
Asp  Arg  Gly  Leu  Thr
 1                  5
```

( 2 ) INFORMATION FOR SEQ ID NO:8:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:8:

```
Thr  Arg  Pro  Gly  Ser  Gly  Leu  Thr  Asn  Ile
 1                  5                         10
```

( 2 ) INFORMATION FOR SEQ ID NO:9:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:9:

Lys  Thr  Glu  Glu  Ile  Ser  Glu  Val  Lys  Met
   1                 5                      10